United States Patent [19]
Commereuc

[11] Patent Number: 5,596,115
[45] Date of Patent: Jan. 21, 1997

[54] COMPOUNDS OF RHENIUM AND ALUMINIUM, PREPARATION THEREOF AND USE THEREOF AS CATALYSTS

[75] Inventor: Dominique Commereuc, Meudon, France

[73] Assignee: Institut Francais Du Petrole, France

[21] Appl. No.: 554,352

[22] Filed: Nov. 6, 1995

[30] Foreign Application Priority Data

Nov. 4, 1994 [FR] France .................. 94 13348

[51] Int. Cl.⁶ .................. C07F 13/00; C07F 5/06
[52] U.S. Cl. .................. 556/27; 502/150; 502/171; 585/500; 585/646; 556/45
[58] Field of Search .................. 556/27; 502/150, 502/171; 585/500, 646

[56] References Cited

U.S. PATENT DOCUMENTS 4,454,368 6/1984 Banks .................. 585/646
5,135,958 8/1992 Radlowski et al. .................. 518/728

FOREIGN PATENT DOCUMENTS 0444265 9/1991 European Pat. Off. .
4009910 10/1991 Germany .

*Primary Examiner*—Porfirio Nazario-Gonzalez
*Attorney, Agent, or Firm*—Millen, White, Zelano, & Branigan, P.C.

[57] ABSTRACT

The present invention concerns new compounds of rhenium and aluminum corresponding to the general formula: $O_3Re-O-[Al(OR)(L)_x-O]_n-ReO_3$ in which R is a hydrocarbyl residue, for example alkyl, cycloalkyl, alkenyl, aryl and aryl or cycloalkyl which are substituted, containing from 1 to 40 carbon atoms, which residue can be substituted by alkoxy groups or by halogens, L is the synthesis solvent, x is equal to 0 or 1 and n is an integer of from 1 to 10. The invention also concerns derived compounds of the formula $O_3Re(L')-O-[Al(OR)(L)_x-O]_n-ReO_3(L')$ in which L' is a stabilising ligand. The invention also concerns the preparation of such compounds and the use thereof in the preparation of catalysts.

20 Claims, No Drawings

COMPOUNDS OF RHENIUM AND ALUMINIUM, PREPARATION THEREOF AND USE THEREOF AS CATALYSTS

The invention concerns new catalytic compounds of rhenium and aluminium, the preparation thereof and the use thereof as catalysts, in particular for the metathesis of olefins in the homogeneous phase.

There are not many soluble compounds of rhenium which are capable of catalysing in a homogeneous phase the metathesis reaction of olefins. It is moreover essential, in order to promote the activity thereof, to associate them with a co-catalyst, in most cases a compound of aluminium or tin, having alkylating and/or Lewis properties. By way of example mention may be made of rhenium pentachloride $ReCl_5$ associated with tetrabutyltin (J. A. Moulijn et al, J Chem Soc Chem Comm, 1971, page 1170) or with triethylaluminium in the presence of oxygen (Y. Uchida et al, Bull Chem Soc Japan, Vol 45, 1972, page 1158), its derivatives such as $ReCl_4(PPh_3)$ and $ReOCl_3(PPh_3)_2$ which are associated with dichloroethylaminium (French patent No. 1 561 025), rhenium pentacarbonyl chloride $Re(CO)_5)Cl$ associated with dichloroethylaluminium (M. F. Farona et al, Inorg Chem, Vol 15, 1976, page 2129), dirheniumdecarbonyl $Re_2(CO)_{10}$ in the presence of dichloroisobutylaluminium as co-catalyst (S. Warwel et al, Makromol Chem Rapid Comm, Vol 4, 1983, page 423), methyl trioxorhenium $CH_3ReO_3$ associated with a chloroalkylaluminium or with a mixture of aluminium chloride and tetramethyltin (W. A. Hermann et al, Angew Chem Int Ed Engl, Vol 30, 1991, page 1636, and Vol 27, 1988, page 394).

The object of the present invention is to describe new compounds of rhenium and aluminium, which are soluble in a hydrocarbon medium and are in themselves active for catalysis, and in particular to catalyse the methathesis reaction without any necessity (in most cases) to add a co-catalyst thereto.

Those new compounds of rhenium and aluminium correspond to the following general formula:

$$O_3Re-O-[Al(OR)(L)_x-O]_n-ReO_3 \quad (A)$$

wherein R is a hydrocarbyl residue, for example alkyl, cycloalkyl, alkenyl, aryl, and aryl or cycloalkyl which are substituted by at least one alkyl group, R containing from 1 to 40 carbon atoms, preferably a hydrocarbyl residue with from 2 to 30 carbon atoms, which residue can be substituted by at least one alkoxy group or by at least one halogen, L is the synthesis solvent, x is equal to 0 or 1 and n is an integer of from 1 to 10. By way of example, and without the following list being limitative, R may be an ethyl, n-propyl, isopropyl, n-butyl, t-butyl, cyclohexyl, benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenyl, 2-t-butyl-4-methylphenyl, 2,6-di-t-butylphenyl, 2,6-di-t-butyl-4-methylphenyl, 2,4,6-tri-t-butylphenyl, 2-phenylphenyl, 2,6-diphenylphenyl, 2-fluorophenyl, 4-fluorophenyl and pentafluorophenyl residue.

The solvent L will be defined hereinafter in the description of a preparation process.

The consequence of the catalytic activity of those compounds of rhenium and aluminium (in particular in the methathesis of olefins) is instability thereof when the attempt is made to isolate them. In order to characterise them it is necessary to stabilise them by the addition of suitable ligands at the end of their synthesis. The stabilised compounds which are inactive in respect of catalysis correspond to the following general formula:

$$O_3Re(L')-O-[Al(OR)(L)_x-O]_n-ReO_3(L') \quad (B)$$

wherein L' is a stabilising ligand selected from the compounds comprising at least one atom of oxygen, sulphur, nitrogen, phosphorous or arsenic, for example, an ether such as diethylether, 1,2-dimethoxyethane or tetrahydrofuran, a sulphide such as tetrahydrothiophene, an amine such as triethylamine, pyridine, 2,2'-bipyridine or N,N,N',N'-tetramethylethylenediamine, a phosphine such as triphenylphosphine or 1,2-bis(diphenylphosphino)ethane. R, L, x and n have been defined in the expression of the formula of compound A.

The identification of the stabilised compounds B makes it possible to characterise the compounds A a posteriori: the formula of A is deduced from that of B by abstraction of the stabilising ligand L'. Moreover, by de-co-ordination of L', the compound A can be obtained from compound B.

The compounds of rhenium and aluminium according to the invention are synthesised by the reaction between rhenium heptoxide $Re_2O_7$ and at least one compound of aluminium of the formula $(RO)_qAlR'_r$ wherein R is defined as above, R' is an alkyl residue containing from 1 to 20 carbon atoms, for example 1 to 6 carbon atoms, for example methyl, ethyl or isobutyl, q and r are equal to 1 or 2 in such a way that the sum q+r is equal to 3.

The reaction is effected in a solvent L referred to as the synthesis solvent, which is preferably anhydrous and which is selected from the group formed by aliphatic or aromatic hydrocarbons such as for example pentane, hexane, benzene, toluene, halongated hydrocarbons such as for example dichloromethane, chlorobenzene, ethers such as for example diethylether, diisopropylether, 1,2-dimethoxyethane, tetrahydrofuran or sulphides such as tetrahydrothiophene. As ether is preferably used. Said solvent L as defined may be included in the general formula of compounds A.

The molar ratio between the aluminium compound and the rhenium may be selected at from 0.2:1 to 10:1. A ratio of 0.5:1 to 5:1 is preferably used. The order in which the reactants are introduced is not critical, however it is preferable for the aluminium compound to be introduced into the solution or the suspension of rhenium heptoxide.

Preparation of the compound $(RO)_qAlR'_r$ is known to the man skilled in the art. Any process for the preparation of that compound is suitable for example by the reaction of a compound $AlR'_3$ with a compound ROH, R and R' being as defined above, the reaction advantageously occurring in a solvent L. The compound prepared in that way is brought into contact with rhenium heptoxide. Generally speaking the compound prepared in that way is isolated and then brought into contact with rhenium heptoxide under the conditions described by the invention.

In another embodiment the reactants used to form the compound $(RO)_qAlR'_r$ are simultaneously brought into contact with rhenium heptoxide, without therefore separation of the product $(RO)_qAlR'_r$.

The reaction temperature may be from −80° to +100° C., preferably from −30° to +80° C. When the reaction is concluded the solvent is advantageously at least partially eliminated (for example the solvent is evaporated under vacuum) and the (evaporation) residue is extracted by a solvent $L_1$, for example preferably an aliphatic, aromatic or cycloaliphatic hydrocarbon, or again a halogenated hydrocarbon or a nitro derivative, such as for example advantageously pentane, heptane, benzene or toluene. The extraction solution can be used directly for catalysis, for example for methathesis catalysis.

In an alternative form the solution obtained containing the compound A is used directly as the catalytic composition.

Previous separation of the solvent is also possible in that case.

If there is a wish to isolate a stable compound B which makes it possible a posteriori to characterise the compound A present in the extraction solution, the ligand L' as defined above is added thereto, and the stabilised compound B is separated by any usual method, for example by precipitation or crystallisation.

This invention also concerns the use of these new compounds of rhenium and aluminium for the preparation of catalysts, and in particular catalysts for the metathesis reaction of olefins.

The compounds A can be used as they are in particular as catalysts in the homogeneous phase in the solvent resulting from the preparation thereof. It is also possible to eliminate that solvent by evaporation to replace it by at least one other more advantageous solvent. The compounds A can thus be used in metathesis in a solvent formed by an aliphatic, cycloaliphatic or aromatic hydrocarbon, a halogenated hydrocarbon or a nitro derivative. A hydrocarbon or a halogenated hydrocarbon is preferably used.

It is possible to add to the compound A, although this is not indispensable, at least one co-catalyst having alkylating and/or Lewis acid properties. The co-catalyst may be a compound of aluminium, boron, gallium, tin or lead. By way of example, and without this list being limitative, mention may be made of aluminium trichloride, aluminium tribromide, dichloroethylaluminium, chlorodiethylaluminium, triethylaluminium, methylaluminoxane, isobutylaluminoxane, boron trifluoride, gallium trichloride, gallium tribromide, tetramethyltin, tetraethyltin, tetrabutyltin and tetraethyllead. It is also possible to use those various compounds mixed with each other.

The process for the metathesis of olefins in the presence of the catalyst defined above occurs at a temperature of from $-20°$ to $+200°$ C., preferably from $0°$ to $+100°$ C. under conditions in respect of pressure such that the reactants are maintained at least in the majority thereof (more than 50%) in the liquid phase or in the condensed phase.

The olefins which can be metathesised are monoolefins having 2 to 30 carbon atoms, for example ethylene, propylene, butenes, pentenes, cycloolefins having from 3 to 20 carbon atoms, for example cyclopentene, cyclooctene, norbornene, polyolefins having from 4 to 30 carbon atoms, for example hexa-1,4-diene, octa-1,7-diene, cyclopolyolefins having from 5 to 30 carbon atoms, for example cycloocta-1,5-diene, norbornadiene and dicyclopentadiene.

Other olefins which can be metathesised are monoolefins or polyolefins which are cyclic or straight chain, bearing functional groups such as for example halogens or ester groups. The process can also use in a co-metathesis mode a mixture of the previous olefins.

The following Examples illustrate the invention without limiting the scope thereof.

EXAMPLE 1

Preparation of
bis-(2,6-di-t-butyl-4-methylphenoxy)-isobutylaminium

Using a 250 ml balloon flask in an argon atmosphere and provided with a magnetic stirrer rod, a solution of 2 ml of triisobutylaluminium in 30 ml of pentane is introduced, then a solution of 3.49 g of 2,6-di-t-butyl-4-methylphenol in 40 ml of pentane is injected drop by drop with agitation and at ambient temperature. After about 30 hours of reaction the pentane is evaporated under vacuum and analysis of the remaining white solid indicates that it is essentially formed by bis-(2,6-di-t-butyl-4-methylphenoxy)-isobutylaluminium.

Preparation of the catalyst (compound A1)

Using a 250 ml balloon flask in an argon atmosphere and provided with a magnetic stirrer rod, the procedure involves introducing 2.75 g of rhenium heptoxide $Re_2O_7$ which is dissolved in 40 ml of tetrahydrofuran (THF). The solution is cooled in a solid carbon dioxide-acetone bath and a solution of 2.97 g of bis-(2,6-di-t-butyl-4-methylphenoxy)-isobutylaluminium in 50 ml of tetrahydrofuran is added thereto over a period of 30 minutes. That corresponds to a molar ratio Al:Re of 0.5:1. At the end of the addition operation the temperature is allowed to rise to ambient temperature and agitation is continued for a further period of 2 hours. The solvent is then evaporated under vacuum to obtain a solid grey-black mass which is then extracted five times with 30 ml of pentane. The pentane extraction solution is of a brown-red colour and its evaporation to dryness gives 3.32 g of a brown powder containing the compound A1. That powder is put back into solution in 30 ml of heptane.

Characterisation of the catalyst (compound B1)

4.5 ml of the solution in heptane of the compound A1 prepared above is taken off. The solvent is evaporated to dryness and 10 ml of toluene is added to produce a solution. Added to that solution is 0.11 g of 2,2'-bipyridine (bipy) dissolved in 3 ml of toluene. By cooling to $-20°$ C., 0.1 g of the compound B1 is obtained in the form of black microcrystals. Analysis by NMR $^1$H ($CD_2Cl_2$): $\delta[C(CH_3)_3]=1.40$ (s), $\delta(p-CH_3)=2.23$, $\delta(C_6H_2)=6.95$, $\delta$(co-ordinated bipy)= 7.32–7.81–8.41–8.64 ppm. Elementary analysis: C=47.46; H=5.66; N=3.17; Al=4.33; Re=26.4% by weight, calculated for B1: $O_3Re(bipy)$—O—$[Al(OC_6H_2$—$CH_3$—(t-$C_4H_9)_2)(THF)$—$O]_2$—$ReO_3(bipy)$: C=47.54; H=5.33: N=3.82; Al=3.69; Re=25.4% by weight. It is deduced therefrom that the compound A1 prepared above corresponds to the following formula: $O_3Re$—O—$[Al(CO_6H_2$—$CH_3$—(t-$C_4H_9)_2)(THF)$—$O]_2$—$ReO_3$.

EXAMPLE 2

Use of the compound A1 in catalysis for the
metathesis of pent-2-ene 6.3 ml of the solution in heptane of the compound A1 prepared in Example 1 is taken off and transferred into a 100 ml balloon flask which is in an argon atmosphere and equipped with a magnetic stirrer rod. 14 ml of heptane is added thereto and the flask is immersed in a thermostatically controlled bath at 25° C. 5 ml of pent-2-ene (cis+trans mixture) is then injected into that solution. After 1 hour of reaction conversion of the pent-2-ene is 50%. The reaction is therefore complete since maximum conversion at thermodynamic equilibrium is 50%. The products are constituted solely by cis and trans but-2-enes and cis and trans hex-3-enes, in a butenes:hexenes molar ratio of 1:1.

EXAMPLE 3

Preparation of the catalyst (compound A2)

The bis-(2,6-di-t-butyl-4-methylphenoxy)-isobutylaluminium is prepared using the mode of operation described in Example 1. Using a 250 ml balloon flask which is disposed in an argon atmosphere and provided with a magnetic stirrer rod, the procedure involves involving 1.5 g of rhenium heptoxide $Re_2O_7$ which is dissolved in 25 ml of tetrahydrofuran. The solution is cooled in a solid carbon dioxide-acetone bath and added thereto over a period of 30 minutes is a solution of 3.24 g of bis-(2,6-di-t-butyl-4-methylphenoxy)-isobutylaluminum in a 45 ml of tetrahydrofuran. That corresponds to an Al:Re molar ratio of 1:1. At the end of the addition operation the temperature is allowed to rise to ambient temperature and agitation is continued for a further 2 hours. The solvent is then evaporated under vacuum to give a solid grey-black mass which is then extracted five times with 30 ml of pentane. The solution from pentane extraction is of a brown-red colour and evaporation thereof to dryness gives 3.57 g of a dark brown powder containing the compound A2. That powder is put back into solution in 30 ml of heptane.

Characterisation of the catalyst (compound B2)

11 ml of solution in heptane of the compound A2 prepared above is taken off. The solvent is evaporated to dryness and 5 ml of toluene is used to produce a solution. 0.41 g of 2,2'-bipyridine dissolved in 5 ml of toluene is added to that solution. By cooling to −20° C., 0.2 g of the compound B2 is obtained in the form of black micro-crystals. Analysis of NMR $^1H$ ($CD_2Cl_2$): $\delta[C(CH_3)_3]$=1.46 (s), $\delta(p-CH_3)$=2.29, $\delta(C_6H_2)$=7.01, $\delta$(co-ordinated bipy)=7.85–8.46–8.68 ppm. Elementary analysis: C=51.57; H=6.22; N=3.52% by weight, calculated for B2: $O_3Re(bipy)$—O—[Al($OC_6H_2$—$CH_3$—(t-$C_4H_9$)$_2$)(THF)—O]$_3$—$ReO_3$(bipy): C=51.39; H=6.06; N=3.11% by weight. It is deduced therefrom that compound A2 prepared above corresponds to the formula:

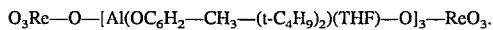

$O_3Re$—O—[Al($OC_6H_2$—$CH_3$—(t-$C_4H_9$)$_2$)(THF)—O]$_3$—$ReO_3$.

EXAMPLE 4

Use of the compound A2 in catalysis for the metathesis of pent-2-ene 3 ml of the solution in heptane of the compound A2 prepared in Example 3 is taken off and transferred into a 100 ml balloon flask which is disposed in an argon atmosphere and equipped with a magnetic stirrer rod. 20 ml of heptane is added thereto and the flask is immersed in a thermostatically controlled bath at 25° C. 5 ml of pent-2-ene (cis+trans mixture) is then injected into that solution. After 1 hour of reaction conversion of the pent-2-ene is 38% (the maximum conversion at thermodynamic equilibrium is 50%). The products are constituted solely by cis and trans but-2-enes and cis and trans hex-3-enes in a butenes:hexenes molar ratio of 1:1.

EXAMPLE 5

Use of the compound A2 in catalysis for the metathesis of pent-2-ene 3.7 ml of the solution in heptane of the compound A2 prepared in Example 3 is taken off and transferred into a 100 ml balloon flask which is placed in an argon atmosphere and equipped with a magnetic stirrer rod. The heptane is evaporated to dryness under vacuum and the residual solid is redissolved in 20 ml of chlorobenzene. The balloon flask is immersed in a thermostatically controlled bath at 25° C. 5 ml of pent-2-ene (cis+trans mixture) is then injected into that solution. After 1 hour of reaction conversion of the pent-2-ene is 50% (the maximum conversion at thermodynamic equilibrium is 50%). The products are formed solely by cis and trans but-2-enes and cis and trans hex-3-enes in a butenes:hexenes molar ratio of 1:1.

EXAMPLE 6

Use of the compound A2 in catalysis for the metathesis of methyl oleate 3 ml of the solution in heptane of the compound A2 prepared in Example 3 is taken off and transferred into a 100 ml balloon flask which is disposed in an argon atmosphere and equipped with a magnetic stirrer rod, 20 ml of heptane is added thereto and the flask is immersed in a thermostatically controlled bath at 25° C. 5 ml of methyl oleate is then injected into that solution. After 1 hour of reaction the conversion of oleate is 16%.

EXAMPLE 7

Use of the compound A2 in catalysis for the polymerisation of cyclopentene by ring opening (polymerisation by metathesis)

20 ml of heptane is introduced into a 100 ml balloon flask which is disposed in an argon atmosphere and equipped with a magnetic stirrer rod and the flask is immersed in a thermostatically controlled bath at 25° C. 5 ml of cyclopentene is then injected, and then 3 ml of the solution in heptane of the compound A2 prepared in Example 3. After 4 minutes of reaction the viscosity of the reaction medium has greatly increased. After 1.5 hours the heptane is evaporated under vacuum and then the product is redissolved with benzene and the polymer is precipitated with methanol. 2.14 g of polymer is collected.

EXAMPLE 8

Use of the compound A2 in catalysis for the polymerisation of norbornene by ring opening 5 ml of heptane is introduced into a 100 ml balloon flask which is disposed in an argon atmosphere and equipped with a magnetic stirrer rod and the flask is immersed in a thermostatically controlled bath at 25° C. 0.97 g of norbornene is then injected, and then 3.5 ml of the solution in heptane of the compound A2 prepared in Example 3. After 30 seconds of reaction the reaction medium is solidified.

EXAMPLE 9

Using a 250 ml balloon flask which is disposed in an argon atmosphere and provided with a magnetic stirrer rod, a solution of 2 ml of triisobutylaluminium in 15 ml of pentane is introduced, and then a solution of 1.95 g of 2,6-diphenylphenol in a mixture of 15 ml of pentane and 20 ml of toluene is injected dropwise with agitation and at ambient temperature. After about 30 hours of reaction the solvent is evaporated under vacuum and the residual white solid is recrystallised from toluene. 1.32 g of product is obtained in the form of white crystals, analysis of which indicates that they are formed by bis-(2,6-diphenylphenoxy)-isobutylaluminium.

Using a 250 ml balloon flask which is disposed in an argon atmosphere and provided with a magnetic stirrer rod, 0.556 g of rhenium heptoxide $Re_2O_7$ is introduced, which is dissolved in 10 ml of tetrahydrofuran. The solution is cooled in a solid carbon dioxide-acetone bath and a solution of 1.32 g of bis-(2,6-diphenylphenoxy)-isobutylaluminium in 15 ml of tetrahydrofuran is added thereto over a period of 30 minutes. At the end of the addition operation the temperature is allowed to rise to ambient temperature and agitation is continued for a further 5 hours. The solvent is then evaporated under vacuum to produce a solid grey-black mass which is then extracted with 15 ml of toluene. The extraction solution is of a dark brown colour and is used directly in catalysis for the metathesis of pent-2-ene.

The flask containing the extraction solution is immersed in a thermostatically controlled bath at 25° C. 3 ml of pent-2-ene (cis+trans mixture) is then injected into that solution. After 1 hour of reaction conversion of the pent-2-ene is 3%. After 4 days of reaction conversion of the pent-2-ene is 29%. The products are formed solely by cis and trans but-2-enes and cis and trans hex-3-enes in a butenes:hexenes molar ratio of 1:1.

EXAMPLE 10

Preparation of the catalyst

Bis-(2,6-di-t-butyl-4-methylphenoxy)-isobutylaluminium is prepared using the mode of operation described in Example 1. Using a 250 ml balloon flask which is disposed in an argon atmosphere and provided with a magnetic stirrer rod, 1 g of rhenium heptoxide $Re_2O_7$ and 30 ml of diethylether are introduced. The solution is cooled in a solid carbon dioxide-acetone bath and a solution of 2.16 g of bis-(2,6-di-t-butyl-4-methylphenoxy)-isobutylaluminium in 30 ml of diethylether is added thereto over a period of 5 minutes. At the end of the addition operation the temperature is allowed to rise to ambient temperature and agitation is continued for a further 2 hours. The solvent is then evaporated under vacuum to give a dark brown solid mass which is then extracted three times with 30 ml of pentane. The pentane extraction solution is of a brown-red colour and evaporation thereof to dryness gives 2.66 g of a dark red powder. That powder is put back into solution in 20 ml of heptane.

Use in catalysis for the metathesis of pent-2-ene 3 ml of the solution in heptane of the compound prepared above is taken off and transferred into a 100 ml balloon flask which is disposed in an argon atmosphere, fitted with a magnetic stirrer rod and immersed in a thermostatically controlled bath at 25° C. 5 ml of pent-2-ene (cis+trans mixture) is then introduced into the flask. After 5 minutes of reaction the conversion of pent-2-ene is 50% (which represents the maximum conversion at thermodynamic equilibrium). The producers are formed solely by cis and trans but-2-enes and cis and trans hex-3-enes.

EXAMPLE 11

Preparation of the catalyst

Bis-(2,6-di-t-butyl-4-methylphenoxy)-isobutylaluminium is prepared using the mode of operation described in Example 1. 1 g of rhenium heptoxide $Re_2O_7$ and 15 ml of diisopropylether are introduced into a 250 ml balloon flask which is disposed in an argon atmosphere and provided with a magnetic stirrer rod. The solution is cooled in a solid carbon dioxide-acetone bath and a solution of 2.16 g of bis-(2,6-di-t-butyl-4-methylphenoxy)-isobutylaluminium in 30 ml of diisopropylether is added thereto over a period of 5 minutes. At the end of the addition operation the temperature is allowed to rise the ambient temperature and agitation is continued for a further 2 hours. The solvent is then evaporated under vacuum to obtain a dark brown solid mass which is then extracted four times with 20 ml of pentane. The pentane extraction solution is of a brown-red colour and evaporation thereof to dryness gives 2.48 g of a dark red powder. That powder is put into solution again in 20 ml of heptane.

Use in catalysis for the metathesis of pent-2-ene 3 ml of the solution in heptane of the compound prepared above is taken off and transferred into a 100 ml balloon flask which is disposed in an argon atmosphere, fitted with a magnetic stirrer rod and immersed in a thermostatically controlled bath at 25° C. 5 ml of pent-2-ene (cis+trans mixture) is then injected into the flask. After 2 minutes of reaction conversion of the pent-2-ene is 47% (maximum conversion at thermodynamic equilibrium is 50%). The products are formed solely by cis and trans but-2-enes and cis and trans hex-3-enes.

I claim:

1. A compound of rhenium and aluminium of the general formula:

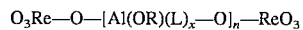

$$O_3Re-O-[Al(OR)(L)_x-O]_n-ReO_3$$

wherein R is a hydrocarbyl residue containing from 1 to 40 carbon atoms, n is an integer of from 1 to 10, x is equal to 0 or 1 and L represents the synthesis solvent.

2. A compound according to claim 1 wherein R is selected from the group formed by the following residues: alkyl, cycloalkyl, alkenyl, aryl, and aryl or cycloalkyl which are substituted by at least one alkyl group.

3. A compound according to claim 1 wherein R is selected from the group formed by the following residues: alkyl, cycloalkyl, alkenyl, aryl, and aryl or cycloalkyl which are substituted by at least one alkyl group, said residues being substituted by at least one alkoxy group or at least one halogen.

4. A compound according to claim 1 wherein R contains from 2 to 30 carbon atoms.

5. A compound according to claim 1 wherein R is selected from the group formed by the following residues: ethyl, n-propyl, isopropyl, n-butyl, t-butyl, cyclohexyl, benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenol, 2-t-butyl-4-methylphenyl, 2,6-di-t-butylphenyl, 2,6-di-t-butyl-4-methylphenyl, 2,4,6-tri-t-butylphenyl, 2-phenylphenyl, 2,6-diphenylphenyl, 2-fluorophenyl, 4-fluorophenyl and pentafluorophenyl.

6. A compound according to claim 1 wherein L is selected from the group formed by aliphatic hydrocarbons, aromatic hydrocarbons, halogenated hydrocarbons, ethers and sulphides.

7. A process for the preparation of a compound according to claim 1 by bringing rhenium heptoxide into contact with at least one compound of aluminium of the formula: $(RO)_qAlR'_r$, wherein R is a hydrocarbyl residue containing from 1 to 40 carbon atoms, R' is an alkyl residue containing from 1 to 20 carbon atoms and q and r are equal to 1 or 2 with q+r=3.

8. A process for the preparation of a compound according to claim 1 by bringing rhenium heptoxide into contact with at least one compound of the formula $AlR'_3$ wherein R' is an alkyl residue containing from 1 to 20 carbon atoms, and with at least one compound of the formula ROH, R being a hydrocarbyl residue containing from 1 to 40 carbon atoms, the reaction occurring in a solvent L.

9. A process according to claim 7 wherein the contacting operation is effected in a solvent L selected from the group formed by aliphatic hydrocarbons, aromatic hydrocarbons, halogenated hydrocarbons, ethers and sulphides.

10. A process according to claim 7 wherein the solvent L is anhydrous.

11. A process according to claim 7 wherein the molar ratio between the aluminium compound and the rhenium is between 0.2:1 and 10:1.

12. A process according to claim 7 wherein the molar ratio between the aluminium compound and the rhenium is between 0.5:1 and 5:1.

13. A process according to claim 7 wherein the temperature is −80° to 100° C.

14. A process according to claim 7 wherein the temperature is from −30° to 80° C.

15. A process according to claim 7 wherein R' contains from 1 to 6 carbon atoms.

16. A process according to claim 7 comprising preparation of the compound $(RO)_q AlR'_r$ and then contacting said compound which has been previously isolated with rhenium heptoxide.

17. A process according to claim 7 comprising, after the contacting operation, at least partial elimination of the solvent present in the contacting operation and extraction of the residue obtained by another solvent $L_1$.

18. A stable compound of rhenium and aluminium of the general formula:

$$O_3Re(L')-O-[Al(OR)(L)_x-O]_n-ReO_3(L')$$

wherein R is a hydrocarbyl residue containing from 1 to 40 carbon atoms, n is an integer of from 1 to 10, x is equal to 0 or 1, L representing the synthesis solvent, and L' is a stabilising ligand selected from the group formed by the compounds comprising at least atom of oxygen, sulphur, nitrogen, phosphorous or arsenic.

19. A compound according to claim 18 wherein L' is selected from the group formed by ethers, sulphides, amines and phosphines.

20. In a catalytic process for the metathesis of a compound having an olefinic double bond, the improvement comprising employing as the catalyst, a compound according to claim 1.

* * * * *